US005466798A

United States Patent [19]
Singaram et al.

[11] Patent Number: 5,466,798
[45] Date of Patent: Nov. 14, 1995

[54] SYNTHESIS OF LITHIUM AMINOBOROHYDRIDES AND REACTIONS THEREOF

[75] Inventors: Bakthan Singaram, Santa Cruz; Gary B. Fisher, Boulder Creek; Joseph C. Fuller; John Harrison, both of Santa Cruz, all of Calif.; Christian T. Goralski, Midland, Mich.

[73] Assignee: The Regents of the University of California, Oakland, Calif.

[21] Appl. No.: 138,612

[22] Filed: Oct. 15, 1993

Related U.S. Application Data

[63] Continuation of Ser. No. 848,427, Mar. 6, 1992, abandoned, which is a continuation-in-part of Ser. No. 847,171, Mar. 6, 1992, abandoned.

[51] Int. Cl.$^6$ ............ C07D 223/02; C07D 207/00; C07F 5/02
[52] U.S. Cl. ............ 540/541; 544/69; 546/13; 548/405; 556/7; 556/8; 564/9; 423/179.5; 423/194
[58] Field of Search ............ 564/9; 423/179.5, 423/194; 540/541; 546/13; 548/405; 556/7, 8

[56] References Cited

U.S. PATENT DOCUMENTS

| 4,886,924 | 12/1989 | Goralski | 358/318 |
| 4,895,996 | 1/1990 | Goralski | 565/328 |

FOREIGN PATENT DOCUMENTS

| 60-149593A | 8/1985 | Japan | 564/9 |

OTHER PUBLICATIONS

Hutchins et al., J. Org. Chem., 1984, 49, 2438–2443.
Brown et. al, J. Am. Chem. Soc., 78, 1956, 3614.
Strouf et. al, Acta Chemica Scandinavica A 31 (1977) 391–401.
Keller, Inorganic Chemistry, vol. 14, No. 2, 1975, 438–440.
Keller, Inorganic Chemistry, vol. 14, No. 2, 1975, 440.
H. C. Brown et al., 1982, *Organometallic Chemistry*, vol. 239, p. 43. "Investigations in the Synthesis of Alkyl–substituted Borohydrides".
B. Singaram et al., 1991, *Journal of Organic Chemistry*, vol. 56, p. 5691. "Unusual Directive Effects in the Hydroboration of B,B–Disubstituted Enamines. Conversion of α–Substituted Aldehydes to the Corresponding Alkenes and B–Amino Alcohols".
E. R. H. Walker, *Chemical Society Review*, 1976, vol. 5, p. 23. "The Functional Group Selectivity of Complex Hydride Reducing Agents".
A. L. Allred et al., 1958, *Journal of Inorganic Nuclear Chemistry*, vol. 5, p. 264. "A Scale of Electronegativity Based on Electrostatic Force".
F. A. Davis et al., 1971, *Journal of Organic Chemistry*, vol. 36, p. 1300. "The Effect of Alkyl Substitution on the Boron–11 Chemical Shifts in Aminoboranes and Borates".
H. C. Brown, et al., 1984, *Journal of Organic Chemistry*, vol. 49, p. 885. "Selective Reductions. 33. Potassium Triisopropoxyborohydride as a Selective Reducing Agent in Organic Synthesis. reaction with Selected Organic Compounds Containing Representative Functional Groups".
E. R. Garret et al., 1953, *Journal of American Chemical Society*, vol. 75, p. 6051. "The Kinetics of 20–Keto reduction in 11α–Acetoxypregnane–3,20–dione by Sodium Borohydride".
H. Haubenstock et al., 1962, *Journal of American Chemical Society*, vol. 84, p. 2368. "Reductions with Metal Hydrides. XI. Solvent Effect on the Stereochemistry of Reduction with Sodium Borohydride".
H. C. Brown et al., 1953, *Journal of the American Chemical Society*, vol. 75, p. 6263. "Addition Compounds of Alkali Metal Hydrides. II. Sodium Trimethoxyborohydride as a Reducing Agent for Organic Compounds".
C. A. Brown, et al., 1973, *Journal of the Chemical Society, Chemical Communications*, 1973, p. 391. "Potassium Tri–isopropoxyborohydride. A New Mild Complex Hydride Reducing Agent with High Stereoselectivity for Reduction of Ketones".
J. H. Golden, et al., 1992, *Inorganic Chemistry*, vol. 31, p. 1533. "Disproportion of Alkoxyborohydrides: A $^{11}$B NMR Study of the Reaction between Sodium Borohydride and Fluorinated Alcohols and Phenols. The Preparation of Tris(fluoroalkoxy)– and Tris(fluorophenoxy)borohydrides".
B. Singaram et al., *J. of Org. Chem.*, 1991, vol. 56, p. 5691. "Unusual Directive Effects in the Hydroboration of beta, beta–Disubstituted Enamines. Conversion of alpha–Substituted Aldehydes to the Corresponding Alkenes and beta–Amino Alcohols".
A. Hajos, *Complex Hydrides*, 1979, Pub.: Elsevier, New York, N.Y. Common reference book; title page and Table of Contents included.
C. T. Goralski et al. *J. of Org. Chem.*, 1987, vol. 52, p. 4014. "Hydroboration. 81. Synthesis of 2–(Dialkylamino)boronic Esters and Acids via Hydroboration of Enamines. A convenient Preparation of beta–Dialkylamino Alcohols".
H. C. Brown et al., *Accounts of Chem. Research*, vol. 21, No.

(List continued on next page.)

Primary Examiner—Shailendra Kumar
Attorney, Agent, or Firm—Phillips Moore Lempio & Finley

[57] ABSTRACT

The present invention relates to novel, powerful reducing agents, lithium aminoborohydrides which are prepared by addition of $BH_3 \bullet THF$ to the corresponding dialkylamine at 25° C. to give the intermediate aminoborane complex. Subsequent deprotonation by strong base, e.g. n-BuLi, yields the aminoborohydride quantitatively. Lithium aminoborohydrides are powerful reducing agents, comparable in strength to lithium aluminum hydride. The activity is determined by the dialkylamine. Lithium pyrrolidinoborohydride has unique activity and selectivity in its reducing properties. Esters, lactones and anhydrides are reduced cleanly at 25° C. to give the corresponding alcohols, while carboxylic acids are not reduced. Test reductions show that lithium pyrrolidinoborohydride is also capable of reducing a wide range of functional groups including amides, epoxides, oximes, nitriles and halides.

12 Claims, 1 Drawing Sheet

OTHER PUBLICATIONS

8, Aug. 1988, p. 287. "Development of a Simple General Procedure for Synthesis of Pure Enantiomers via Chiral Organoboranes".

B. Singaram et al., *J. of Org. Chem.*, 1991, vol. 56, p. 1543. "Hydroboration. 86. Convenient Conversion of Aldehydes and Ketones into the Corresponding Alkenes via Hydroboration of the Enamines".

FIGURE I
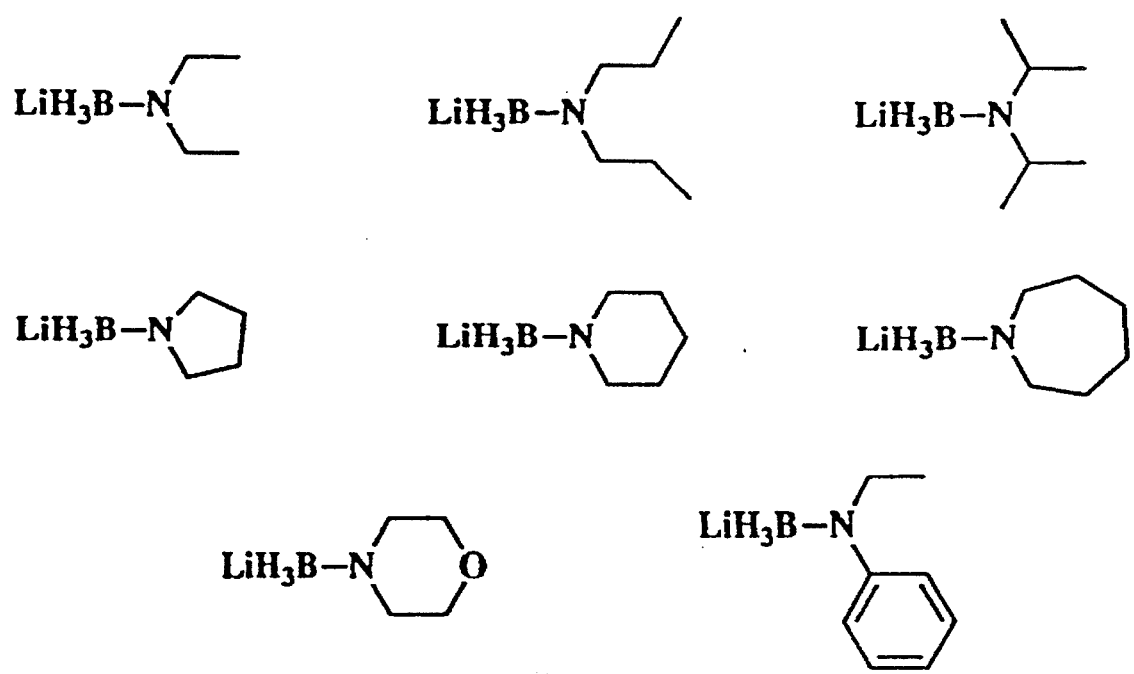

SYNTHESIS OF LITHIUM AMINOBOROHYDRIDES AND REACTIONS THEREOF

This is a continuation of application of Ser. No. 07/848, 427 filed on Mar. 6, 1992, now abandoned, which is a continuation-in-part of the application Ser. No. 07/847,171 filed on Mar. 6, 1992, now abandoned.

BACKGROUND OF THE INVENTION

1. Source of the Invention

This invention was made with support under Dow Chemical Company Contract No. 443120-57276-3. Dow Chemical Company may have some rights in this invention.

2. Field of the Invention

The present invention relates to the synthesis of novel lithium aminoborohydrides, and to their use as a powerful selective reducing agents for organic compounds.

3. Description of Related Art

A commercially safe, economical reducing agent has been the goal of a number of academic and industrial groups. Some art of general interest is as follows:

C. T. Goralski et al., U.S. Pat. No. 4,886,924.

C. T. Goralski et al., U.S. Pat. No. 4,895,996.

H. C. Brown et al. (1988), *Accounts for Chemical Research*, Vol. 21 (#8), p. 287.

More specific references are described below and are referred to in the subsequent text as (Ref. 2) or (2a), etc.

References of interest include:

1. (a) E. R. H. Walker, (1976) *Chem. Soc. Rev.*, Vol. 5, p. 23;
  (b) A. Hajos, (1979) *Complex Hydrides*, Elsevier: N.Y.
2. (a) H. C. Brown et al., (1956) *J. Am Chem. Soc.*, Vol. 78, p. 3616;
  (b) H. C. Brown et al., (1953) *Ibid.*, Vol. 73, p. 6263;
  (c) C. A. Brown et al., (1973) *J. Chem. Soc. Chem. Comm.*, 391.
3. J. H. Golden et al. (1992), *Inorg. Chem.*, Vol. 31, 0000.
4. H. C. Brown et al. (1984), *J. Org. Chem.*, Vol. 49, p. 885.
5. (a) E. R. Garret et al. (1953), *J. Am. Chem. Soc.*, Vol. 73, p. 6051;
  (b) H. Habenstock et al. (1962), *Ibid.*, Vol. 84, p. 2368.
6. A. L. Allred et al. (1958), *J. Inorg. Nucl. Chem.*, Vol. 5, p. 264.
7. F. A. Davis et al. (1971), *J. Org. Chem.*, Vol. 36, p. 1300.
8. R. O. Hutchins et al. (1984), *J. Org. Chem.*, Vol. 49, p. 2438.
9. H. C. Brown et al. (1982), *Organomet. Chem.*, Vol. 239, p. 43.
10. B. Singaram et al. (1991), *J. Org. Chem.*, Vol. 56, p. 5691.
11. Hutchins et al. (Ref. 8) report a $^{11}$B-NMR chemical shift value of δ+43 for lithium dimethylaminoborohydride. The values obtained in our study differ considerably from that reported by Hutchins et al.

All patents, patent applications, articles, references, standards, cited in this application are incorporated by reference.

Substitution of one or more of the hydrogen atoms on a borohydride with electron donating groups, such as alkoxy or alkyl groups, has attracted considerable interest over the past decade as a method of fine-tuning the hydride delivering ability of the borohydride moiety (Ref. 1). Although borohydrides with three alkoxy groups are known (Ref. 2), borohydrides with one or two alkoxy groups are at best fleeting intermediates (3). Trialkoxyborohydrides are very mild reducing agents (4). This result is unexpected because hydride transfer would be expected to be more difficult from a stronger Lewis acid, such as $BH_3$, than from a weaker Lewis acid, such as $(RO)_3B$, a compound weakened by back bonding (5). The inductive effect of the alkoxy group may predominate over the mesomeric effect. Monoalkoxy substituted borohydrides may, therefore, be even better reducing agents. However, no monoalkoxyborohydrides have ever been reported.

One type of heteroatom-substituted borohydride that potentially may have useful characteristics are the aminoborohydrides. Because of the lower electronegativity of nitrogen compared to oxygen (3.07 vs. 3.50) (6), better donation of the lone pair of electrons toward the boron atom from the nitrogen atom may be possible. Consequently, aminoborohydrides might have enhanced hydride delivering ability compared to either borohydride or the trialkoxy derivative. Moreover, aminoboranes are weaker Lewis acids than $BH_3$ or $(RO)_3B$ (7). These properties suggest that once produced aminoborohydrides should be better reducing agents. This result was demonstated recently by the synthesis of sodium dimethylaminoborohydride and the study of its reduction characteristics (8). The aminoborohydride was prepared by the reaction of sodium hydride with dimethylamine borane (e.g. reaction sequence 1) (Ref. 8).

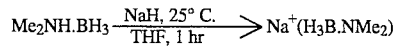

Sodium dimethylaminoborohydride showed enhanced reducing ability. Thus, it not only reduced aldehydes and ketones to corresponding alcohols, but was also found to be an effective reagent for the conversion of esters to alcohols and primary amides to amines. Tertiary amides were reduced to either alcohols or amines, depending on the steric requirements of the amide group. It is known that the reactivity of the borohydrides decreases rapidly in the series lithium borohydride>sodium borohydride>potassium borohydride (9). Consequently, lithium aminoborohydrides, when obtained, would be expected to be more powerful reducing agents than the corresponding sodium derivatives.

At this time, the synthesis of novel lithium aminoborohydrides has not been described. Further, the use of these novel hydrides as powerful reducing agents has not been reported. The present invention provides a synthesis of lithium aminoborohydrides and their use as powerful reducing agents.

SUMMARY OF THE INVENTION

The present invention relates a process for the synthesis of lithium aminoborohydride of the structure:

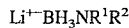

wherein $R^1$ and $R^2$ are each independently chiral or achiral groups selected from alkyl having from 1 to 20 carbon atoms;

aryl having from 6 to 20 carbon atoms;

$R^1$ and $R^2$ together form a cyclic ring having from 4 to 10 carbons having the nitrogen atom in the ring, or $R^1$ and $R^2$ together form a ring structure having from 4 to 10 carbon atoms, nitrogen in the ring, and also have a second heteroatom selected from sulfur, nitrogen or oxygen atom in the ring;

which process comprises:

(a) contacting an amine of the structure

H NR¹R² wherein R¹ and R², are defined hereinabove with a borane selected from:

BH₃·•A, R⁴BH₂ or, R⁴R⁵BH or mixtures thereof wherein R⁴ and R⁵ are each independently selected from chiral or achiral alkyl groups having 1 to 20 carbon atoms or aryl having 6 to 12 carbon atoms, wherein A is an adduct selected from tetrahydrofuran, tetrahydropyran, dioxane, dialkyl sulfide $(R^6)_2S$ wherein $R^6$ is selected from alkyl having 1 to 6 carbon atoms, thiophene, tetrahydrothiophene, 1,4-dithiane, 1,4-oxathiane or combinations thereof;

in a dipolar aprotic solvent at a temperature of between about +50° and −50° C. at ambient pressure for a time effective to react with amine;

(b) contacting the reaction product of step (a) with a strong base $R^3$-Li, wherein $R^3$ is selected from alkyl having 1 to 6 carbon atoms or aryl having from 6 to 12 carbon atoms.

The invention also relates to a process to reduce an organic compound which process comprises:

(a) contacting the organic compound selected from an ester, lactone, anhydride, amide, epoxide, oxime, nitrile, acyl halide, alkyl halide or combinations thereof, with a lithium aminoborohydride of claim 1 under anhydrous conditions at between −25 and +50° C. for a time effective to produce the reduced product.

BRIEF DESCRIPTION OF THE FIGURE

FIG. 1 shows representative examples of lithium aminoborohydrides produced by the present invention.

DETAILED DESCRIPTION OF THE INVENTION AND PREFERRED EMBODIMENTS

Definitions

As used herein:

"Alkyl" refers to saturated chiral or achiral hydrocarbon groups having 1 to 20 carbon atoms. Branched and straight chain groups are included. Preferably, 1 to 10 carbons, e.g. methyl, ethyl, propyl or butyl groups are used.

"Aryl" refers to phenyl or naphthyl or the alkyl or halo substituted phenyl or naphthyl having 6 to 20 carbon atoms.

"Chiral organic group" refers to any conventional organic compound having at least one chiral atom, from 6 to 100 carbon atoms (preferably between 6 and 50 carbon atoms) and capable of forming reactive lithium aminoborohydrides. Conventional polynuclear aromatics, alkaloids, terpenoids, steroids, etc. (see, for example, L. F. Fieser, *Topics in Organic Chemistry*, Reinhold Publishing Corp., N.Y., New York, 1963) are preferred.

"Cycloalkyl" refers to cyclic alkyl groups wherein $R^1$ and $R^2$ have 5, 6, etc. carbons in a ring or multiple rings.

"Cycloalkylene" refers to those cyclic groups wherein $R^1$ and $R^2$ have 4 to 20 carbon atoms having the amine atom in the ring.

"Dipolar aprotic liquid or solvent" refers to any of the conventional organic solvents having a dipole and no easily ionizable protons. Examples include, for example, diethyl ether, dipropyl ether, dibutyl ether, pentane, hexane, decane, tetrahydrofuran, dioxane, hexane, cyclohexane, benzene, toluene, diglyme, or combinations thereof. The ethers are preferred.

During the hydroboration of β,β-disubstituted enamines using borane methyl sulfide (BMS), the formation of aminoboranes, $H_2B$-$NR_2$, as by-products (Reaction Sequence 1). (Ref. 11) was observed.

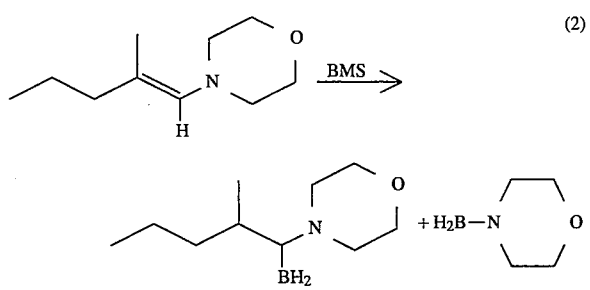

(2)

A general method for synthesizing lithium dialkylaminoborohydrides is described. The reaction of n-butyllithium or methyllithium with borane-amine complexes, e.g. $H_3B$:$NHR_2$, produces the corresponding lithium aminoborohydrides in essentially quantitative yields (Reaction Sequence 3).

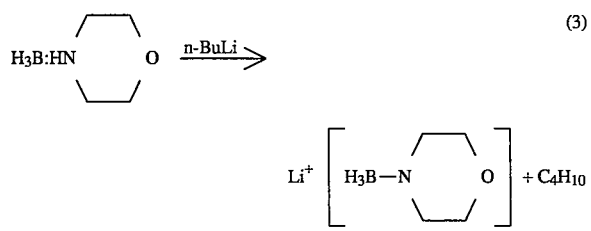

(3)

This reaction is very general and a wide variety of amino groups are possible. Following the general procedure of Reaction Sequence 3, the representative lithium aminoborohydrides as shown in FIG. 1 were prepared.

These lithium aminoborohydrides are very stable compounds, and are stored under nitrogen at 25° C. for six months or more without undergoing any decomposition or loss of hydride activity. More importantly, aminoborohydrides are not pyrophoric and do not react violently with air. They react slowly with methanol or any other acidic compounds which have a $pK_a$ above 4.0.

The lithium aminoboranes are produced as follows:

In an inert atmosphere and anhydrous reaction system is added the organic amine $HNR^1R^2$ and borane adduct $BH_3eA$ (e.g. A=THF). This reaction mixture is stirred at between about −50° and +50° C., preferably 0° to 40° C., and especially at ambient for between about 0.1 and 10 hr, preferably between about 0.5 and 5 hr, and especially about 1 hr in a dipolar aprotic solvent.

The borane may also be $R^4BH_2$ or $R^4R^5BH$ wherein $Rp^4$ and $R^5$ are each independently selected from chrial or achiral alkyl having 1 to 20 carbon atoms or aryl having from 6 to 12 carbon atoms. It is generally known in the art that $R^4BH_2$ or $R^4R^5BH$ may exist as an equilibrium mixture between the monomeric and dimeric species. The monomer when present is optionally complexed with an addduct, A.

To the reaction mixture is added a strong base, e.g $R^3$-Li where $R^3$ is defined hereinabove at between −50° and +50° C., preferably between about −10° and 40° C., more preferably between about −10 and +10° C., especially about 0° C. for between about 0.1 and 10 hr, prefereably between about 0.5 and 5 hr, more preferably between about 1 to 3 hr. During this time period the temperature is allowed to come to ambient. The lithium aminoborohydride is produced in substantially pure form, wherein the purity is about 90% or greater, up to about 100% purity. In Example 1, the compound is 92% pure. It is not necessary to isolate the lithium aminoborohydide from the solvent.

The lithium aminoborohydride formed is added to an organic compound having a reduceable group, e.g. a carbonyl, in an anhydrous dipolar aprotic solvent at between about 0° to 50° C., preferably about ambient, for between about 1 and 48 hr, preferably between about 2 and 30 hr. The reduced organic compound (usually an alcohol) amine or hydrocarbon is recovered and subjected to conventional recovery procedures for organic compounds where $R^3$ is defined hereinabove.

Lithium pyrrolidinoborohydride is useful to evaluate the reduction characteristics of these aminoborohydrides. The procedure used involves the preparation of a reaction mixture of lithium pyrrolidinoborohydride (1.3M., 4.0M in hydride), and the organic unsaturated compound (0.25M) under study in tetrahydrofuran (THF) at 25° C. The solution obtained is maintained at 25° C. Aliquots are periodically removed from the reaction mixture and analyzed by hydrolysis for the remaining hydride. The amount of hydride used by the compound for reduction is calculated from the volume of hydrogen evolved. Initial results indicate that lithium pyrrolidinoborohydride is a very powerful reducing agent, comparable in reducing power to lithium aluminum hydride, i.e. it reduces aldehydes, ketones, esters, lactones, acid chlorides, acid bromides, acid iodides, anhydrides, amides, epoxides, oximes, nitriles, alkyl chlorides, alkyl bromides, or alkyl iodides. Only organic carboxylic acids appear to not be subject to reduction by this novel reducing agent. The nitrogen containing groups are usually reduced to amines. The alkyl halides become hydrocarbons.

After initial pilot reductions, isolation-scale reductions are carried out on representative substrates. Successful product isolations are found to require prior acid hydrolysis to eliminate contamination by boron-containing materials. The products from these large-scale reactions were easily isolable in both high yield and high purity. Benzoic acid is recovered unreduced; however, both aliphatic and aromatic esters were reduced to the corresponding alcohols in essentially quantitative yield (see Reaction Sequences 4 and 5 below).

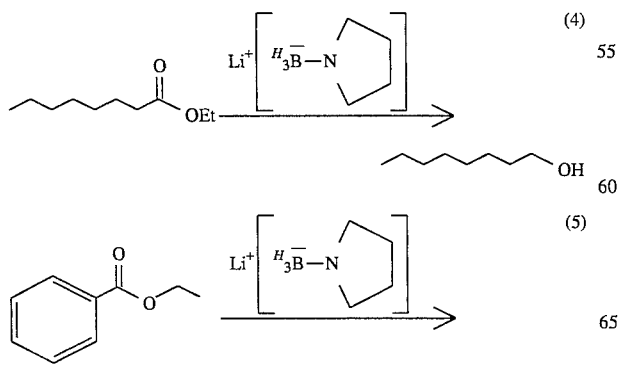

(4)

(5)

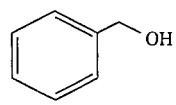

-continued

The reduction of benzaldehyde, acetophenone, and cyclohexanone takes place readily to afford the corresponding alcohols. Cyclohexenone undergoes exclusive 1,2-reduction to produce the corresponding allylic alchohol (Reaction Sequence 6 below).

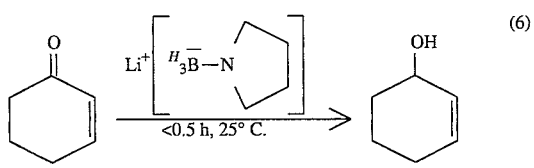

(6)

Epoxides are reduced readily with lithium pyrrolidinoborohydride. Thus, cyclohexene oxide is reduced to cyclohexanol, and styrene oxide gives predominantly 2-phenylethanol (see Reaction Sequences 7 and 8).

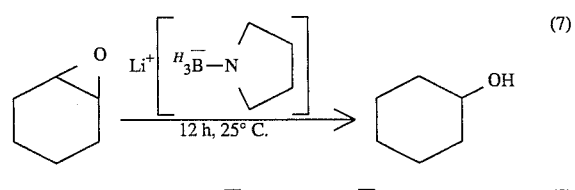

(7)

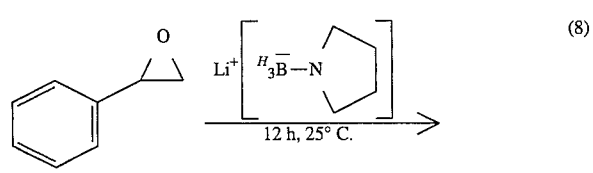

(8)

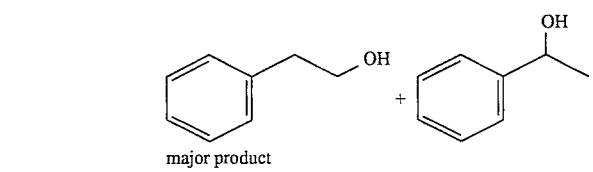

major product

The reduction of N,N-dimethylbenzamide yields benzyl alcohol (Ref. 9). Apparently, after initial nucleophilic attack by hydride, the carbon-nitrogen bond undergoes cleavage, liberating benzaldehyde which is further reduced to produce the observed product (see Reaction Sequence 9 below).

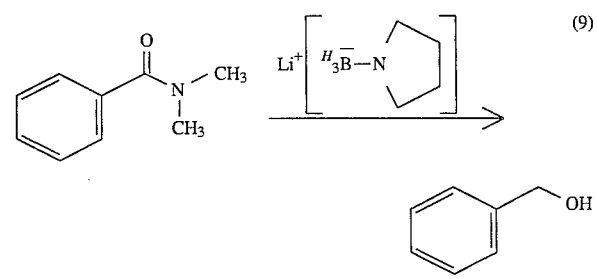

(9)

Lithium aminoborohydrides are readily synthesized by the reaction of the corresponding borane-amine complexes with n-butyllithium. These aminoborohydrides are effective reducing agents for the reduction of aldehydes, ketones, esters, epoxides, and secondary or tertiary amides. However, they do not reduce carboxylic acids or primary amides.

The following Examples are presented to further explain and describe the present invention. They are not to be construed to be limiting in any manner.

General - All operations were carried out under a nitrogen atmosphere. All glassware, syringes and needles were oven-dried at 110° C. and cooled to room temperature with nitrogen gas before use. THF was freshly distilled from sodium and benzophenone ketyl. Anhydrous ether, amines, $BH_3 \bullet THF$, and n-butyllithium were purchased from Aldrich Chemical Company, Milwaukee, Wisconsin, and used directly without further purification $^1$H-NMR, $^{13}$C-NMR and $^{11}$B-NMR were obtained at 250 MHz. Chemical shifts are in $\delta$ units relative to internal tetramethylsilane for hydrogen and carbon and $BF_3 \bullet Et_2O$ for boron.

EXAMPLE 1

SYNTHESIS OF LITHIUM PYRROLIDINOBOROHYDRIDE (a) The following procedure is representative. To a 250-mL side arm round bottom flask equipped with a magnetic stirring bar and sealed with a rubber septum is added, by syringe, pyrrolidine (14.91 g, 17.5 mL, 210 mmol), followed by addition, with stirring, of $BH_3 \bullet THF$ (1M, 210 mL, 210 mmol). The reaction is stirred for 1 hr at 25° C. The reaction mixture is cooled to 0° C. and n-butyllithium is added dropwise by syringe (2.5M, 1.1 eq., 93 mL, 231mmol). The reaction is stirred at 0° C. for 2–3 hr and allowed to come to room temperature. The reaction was stirred for an additional 1 hr at 25° C. The yield (92%) was determined by hydride analysis of the molarity of the final THF/Hexanes solution. $^{11}$B-NMR (THF):$\delta$-23(q).

(b) Similarly, when Example 1 above is repeated except that a stoichiometrically equivalent amount of pyrrolidone is replaced with dimethylamine;

diethylamine;

di-n-propylamine;

diisopropylamine;

dioctylamine;

piperidine;

morpholine;

dicyclohexylamine;

hexamethyleneimine;

ethylphenylamine;

diphenylamine; or chiral groups selected from (S) or (R)-N-alkyl-α-methylbenzylamine, (R,R) or (S,S)-2,5-dimethylpyrrolidine;

(R,R) or (S,S)-2,6-dimethylpiperidine, 2-alkylpyrrolidine, or 2-alkylpiperdine, wherein alkyl is methyl, ethyl, propyl, etc. the corresponding lithium aminoborohydride is obtained usually in near quantitative overall yield. (See Table 1 below).

TABLE 1

SYNTHESIS OF LITHIUM AMINOBOROHYDRIDES

| amine boranes[a] | aminoborohydrides[b] | $^{11}$B-NMR chemical shifts,[c,d] $\delta$ (multiplicity) |
|---|---|---|
| $H_3B:HN$(diethylamine) | $[H_3\bar{B}-N$(diethylamine)$] Li^+$ | −18(q) |
| $H_3B:HN$(diisopropyl-like) | $[H_3\bar{B}-N$(diisopropyl-like)$] Li^+$ | −17(q) |
| $H_3B:HN$(di-t-butyl-like) | $[H_3\bar{B}-N$(di-t-butyl-like)$] Li^+$ | −23(q) |
| $H_3B:HN$(pyrrolidine) | $[H_3\bar{B}-N$(pyrrolidine)$] Li^+$ | −18(q) |
| $H_3B:HN$(piperidine) | $[H_3\bar{B}-N$(piperidine)$] Li^+$ | −16(q) |
| $H_3B:HN$(morpholine) O | $[H_3\bar{B}-N$(morpholine) O$] Li^+$ | −16(q) |
| $H_3B:HN$(hexamethyleneimine) | $[H_3\bar{B}-N$(hexamethyleneimine)$] Li^+$ | −16(q) |
| $H_3B:HN$(N-phenyl) | $[H_3\bar{B}-N$(N-phenyl)$] Li^+$ | −20(q) |

[a]Prepared from $BH_3$:THF and the corresponding amine at 25° C.
[b]Obtained quantatively from the reaction of n-BuLi with $H_3B:NHR_2$ at 0° C., 15 min.
[c]$\delta$-relative to $BF_3$:$OEt_2$ = O.
[d]See Ref. 11.

EXAMPLE 2

REDUCTION WITH LITHIUM PYRROLIDINOBOROHYDRIDE (a) The following procedure is representative. To a 50-mL serum vial equipped with a magnetic stirring bar and sealed with a rubber septum is added, by syringe, anhydrous THF (10 mL) followed by an ester, ethyl benzoate (1.4 mL, 1.5 g, 10 mmol). Lithium pyrrolidinoborohydride (0.97M in THF, 13.4 mL, 13.4 mmol) was added dropwise with stirring at 25° C. The reaction mixture was stirred for an additional 24 hr at 25° C. The reaction mixture was quenched with 3M hydrochloric acid (20 mL, 60 mmol). The aqueous solution was extracted with diethyl ether (2×50 mL) and the combined ether extracts were washed with water (25 mL). The ether solution was dried over anhydrous magnesium sulfate for 48 hr. The solvent was removed in vacuo (6 Torr) to yield crude benzyl alcohol in essentially quantitative yield (1.1 g,>99%).

(b) Similarly when Example 2(a) above is repeated except that the ethylbenzoate is replaced by a stoichiometrically equivalent amount of other esters, lactones, anhydrides, amides, epoxides, oximes, nitriles or acyl halides, alkyl halide, the corresponding reduced product organic alcohol, amine, hydrocarbon is produced in high yield.

(c) Similarly, when Example 2(a) above is repeated except that the ester is replaced by a stoichiometrically equivalent amount of acetophenone, phthalic anhydride, phthaloyllactetone, 2-methylcyclohexanone, valoryl chloride, 1,3-cyclohexenone, ethyl octanoate or propylene oxide, the corresponding organic alcohol is produced in 80% yield or greater. (See Table 2 below)

TABLE 2

REDUCTION OF REPRESENTATIVE SUBSTRATES WITH LITHIUM PYRROLIDINO BOROHYDRIDE[a]

| substrate | product | yield, % |
|---|---|---|
| benzoic acid | No Reaction[c] | 0 |
| ethyl benzoate | benzyl alcohol | >95[d] |
| acetophenone | 1-phenylethanol | >95[d] |
| phthalic anhydride | 1,2-benzenedimethanol | >95[d] |
| phthalide | 1,2-benzenedimethanol | 92[b] |

TABLE 2-continued

REDUCTION OF REPRESENTATIVE SUBSTRATES WITH LITHIUM PYRROLIDINO BOROHYDRIDE[a]

| substrate | product | yield, % |
|---|---|---|
| 2-methylcyclohexanone | 2-methylcyclohexanol | 88[b] |
| valoryl chloride | 1-pentanol | 80[b] |
| 1,3-cyclohexenone | 2-cyclohexenol | 85[b] |
| ethyl octanoate | 1-octanol | 92[b] |

[a]Reductions run at 25° C. Acidifications run at 0° C.
[b]Isolated, distilled yields.
[c]No reaction after 24 hr.
[d]Product purity verified by 60 and 250 MHz 1H- and $^1$H- and $^{13}$C NMR.

While only a few embodiments of the invention have been shown and described herein, it will become apparent to those skilled in the art that various modifications and changes can be made in the synthesis of lithium aminoborohydrides and their use as reducing agents for organic compounds without departing from the spirit and scope of the present invention. All such modifications and changes coming within the scope of the appended claims are intended to be carried out thereby.

We claim:

1. A substantially pure lithium aminoborohydride having a purity of about 92% or higher purity of the structure:

$$Li^{+-}BH_3NR^1R^2$$

wherein $R^1$ and $R^2$ are each moieties selected from:

alkyl having from 2 to 20 carbon atoms;

aryl having from 6 to 20 carbon atoms; and $R^1$ and $R^2$ together form a cyclic ring having 4, 5, or 6 carbon atoms producing a lithium aminoborohydride selected from the group consisting of

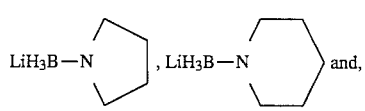

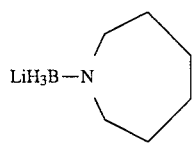

2. The lithium aminoborohydride of claim 1 which is selected from:

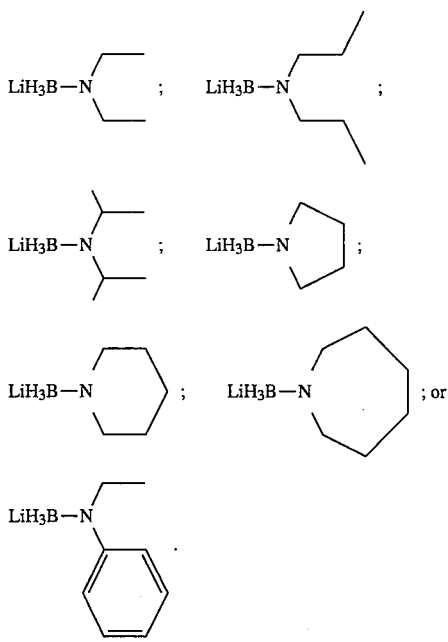

3. The lithium aminoborohydride of claim 1 wherein $R^1$ and $R^2$ are both achiral.

4. The lithium aminoborohydride of claim 1 wherein $R^1$ and $R^2$ are each octyl.

5. The lithium aminoborohydride of claim 2 selected from:

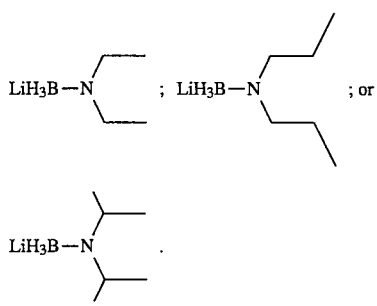

6. The lithium aminoborohydride of claim 2 selected as:

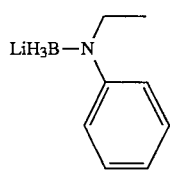

7. The lithium aminoborohydride of claim 1 having the structure:

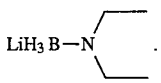

8. The lithium aminoborohydride of claim 1 having the structure:

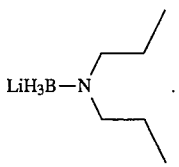

9. The lithium aminoborohydride of claim 1 having the structure:

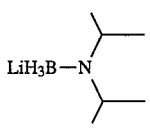

10. The lithium aminoborohydride of claim 1 having the structure:

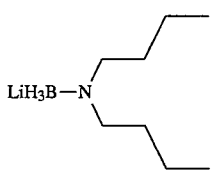

11. The lithium aminoborohydride of claim 1 having the structure:

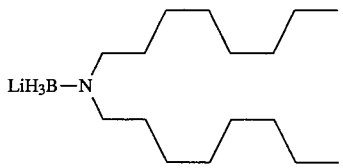

12. The lithium aminoborohydride of claim 2 having the structure:

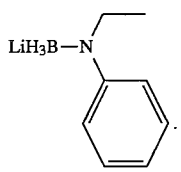

* * * * *